United States Patent [19]

Baier

[11] 4,266,999
[45] May 12, 1981

[54] CATHETER FOR LONG-TERM EMPLACEMENT

[75] Inventor: Robert E. Baier, Buffalo, N.Y.

[73] Assignee: Calspan Corporation, Buffalo, N.Y.

[21] Appl. No.: 61,584

[22] Filed: Jul. 30, 1979

[51] Int. Cl.³ .................... B32B 31/00; A61M 25/00; B29C 19/02

[52] U.S. Cl. ........................... 156/227; 128/348; 156/267; 156/272; 156/278; 156/294; 264/215; 264/216; 264/344; 427/2; 427/40; 427/41; 427/44; 427/181; 427/198; 427/202; 427/271; 427/276; 427/336; 427/401

[58] Field of Search .............. 427/2, 271, 276, 335, 427/336, 40, 41, 44, 430 R, 181, 401, 198, 202, 430.1; 264/344, 215, 216; 128/348; D24/54; 156/227, 272, 267, 294, 278

[56] References Cited

U.S. PATENT DOCUMENTS

| | | | |
|---|---|---|---|
| 3,730,187 | 5/1973 | Reynolds | 128/349 R |
| 3,826,254 | 7/1974 | Mellor | 128/133 |
| 3,866,601 | 2/1975 | Russell | 128/4 |
| 3,908,635 | 9/1975 | Vick | 128/2 M |
| 3,938,529 | 2/1976 | Gibbons | 128/349 R |
| 3,970,090 | 7/1976 | Loiacono | 128/349 R |
| 3,989,571 | 11/1976 | Harautuneian | 156/250 |
| 4,021,382 | 5/1977 | Stoy et al. | 128/349 R |
| 4,043,345 | 8/1977 | Kramann et al. | 128/349 R |
| 4,055,682 | 10/1977 | Merrill | 427/2 |
| 4,100,309 | 7/1978 | Micklos | 427/2 |
| 4,140,127 | 2/1979 | Cianci et al. | 128/349 R |

Primary Examiner—Ronald H. Smith
Assistant Examiner—Janyce A. Bell
Attorney, Agent, or Firm—Biebel, French & Nauman

[57] ABSTRACT

A cannula/catheter is provided which is suitable for long term or semi-permanent through-the-skin function while permitting tissue ingrowth which promotes healing and seals out sources of infection. The catheter is provided with a sheath formed of an elastomeric coating which is glow discharge treated, folded back on itself to form a cuff and surgically implanted and anchored in place. The cuff portion of the sheath is advanced outwardly by the growth of skin adherent to its periphery while the catheter is maintained in its original position.

8 Claims, 16 Drawing Figures

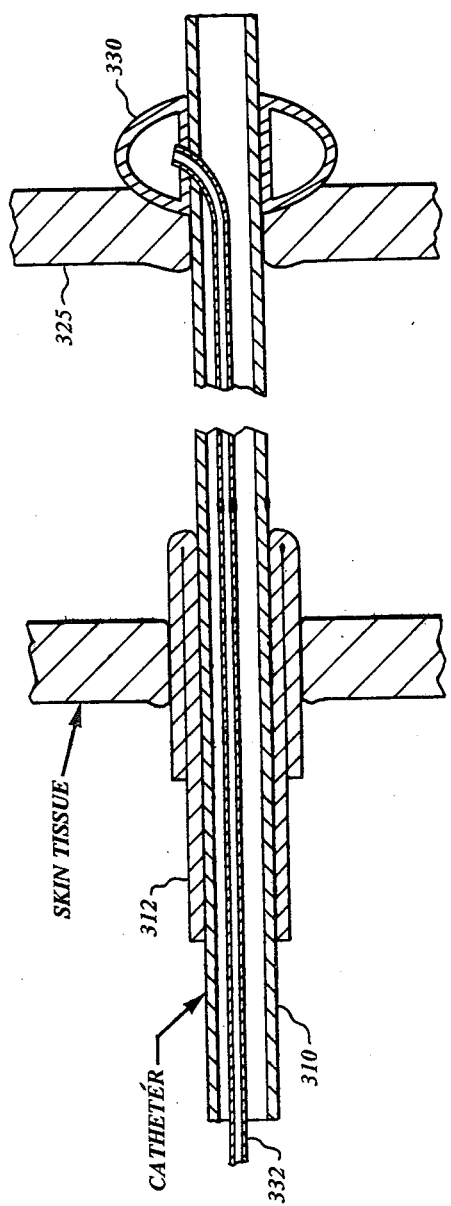
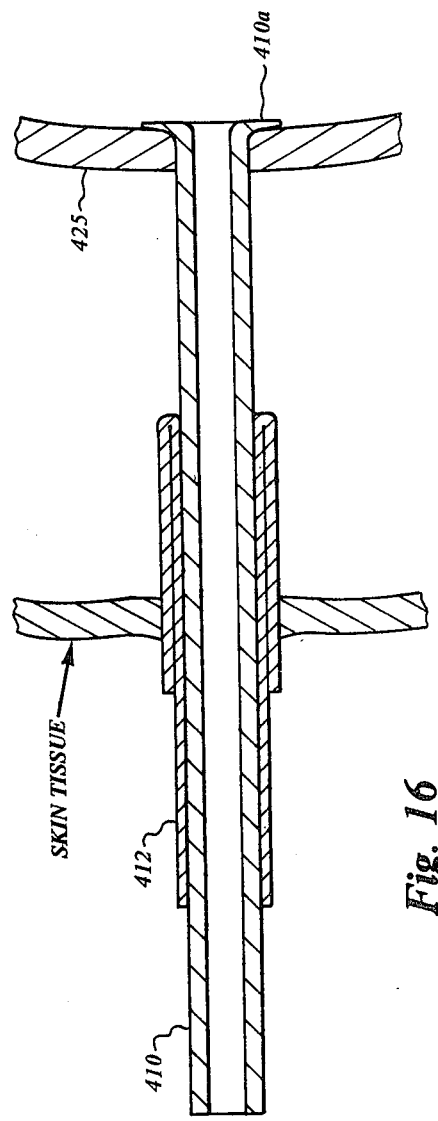
Fig. 15
Fig. 16

CATHETER FOR LONG-TERM EMPLACEMENT

BACKGROUND OF THE INVENTION

Various forms of percutaneous leads have been used in both research and clinical settings for many years. For example, percutaneous synthetic arterio-venous shunts are routinely used in chronic hemodialysis, and percutaneous electrical wires have been used for neurological stimulation (e.g. artificial eye). In most cases an equilibrium state of low grade inflammation results which appears to be tolerated rather well for extended periods of time. The degree of inflammation and the extent to which it is tolerated is related to a number of factors which have, as yet, not been clearly delineated. Certainly the composition of the material, its surface texture, surface chemistry, modulus of elasticity, externally applied forces, mechanical properties, tissue reactivity, size and configuration, site of entry, and method of anchoring are all important.

Heretofore two general approaches have been taken with respect to tissue coaction with cannulae/catheters. At one extreme is the use of velour covered cannulae which elicit aggressive tissue ingrowth. Since tissue growth is roughly at a rate of 1 mm per month, the cannula is extruded outwardly as basal skin cells mature and migrate to the surface. Tissue adherence with a fixed position catheter of this type would cause discomfort to a person due to the tearing of the adhering tissue from the catheter as the tissue grows outwardly. At the other extreme the cannulae are covered with, or made of, inert, nonreactive materials such as silicone rubber or pyrolytic carbon. These inert materials eventually become completely enclosed with an epithelial pocket, resulting in a sinus tract through which bacteria can gain access to underlying tissues. Thus, heretofore good tissue bonding with movement and eventual failure by outgrowth with the living skin at the one extreme or a site of probable infection at the other extreme have been the choices available in the prior art cannulae/catheters intended for long-term emplacement.

SUMMARY OF THE INVENTION

In contrast to the prior art, the present invention provides a catheter that will remain fixed and at the same time permit adhering tissue growth therewith, without causing the aforementioned discomfort. Additionally, the catheter of the present invention does not tend to promote infection as is the case with those which tend to produce a sinus tract.

It is an object of this invention to provide a constant position through-the-skin catheter for percutaneous transmission of energy or matter.

It is a further object of this invention to provide a catheter for long term or semi-permanent through-the-skin placement.

It is an additional object of this invention to provide a fixed position catheter having tissue adherence without causing discomfort.

It is a still further object of this invention to provide a method of preparing a sheath for a catheter.

It is a yet still further object of this invention to provide a percutaneous catheter having long-term freedom from infection, erosion and skin extrusion. These objects, and others as will become apparent hereinafter, are accomplished by the present invention.

The disadvantages of the prior art are overcome according to the teachings of the present invention in which a catheter is provided with a sheath suitable for tissue ingrowth or adhesion thereto. The sheath is glow discharge treated and folded back on itself to form a cuff so that as the adherent tissue/skin growth advances outwardly, the cuff is peeled back exposing new surface areas while leaving the anchored catheter in place.

BRIEF DESCRIPTION OF THE DRAWINGS

For a fuller understanding of the present invention, reference should now be made to the following detailed description thereof taken in conjunction with the accompanying drawings wherein:

FIG. 1 is a pictorial view of a tubular mandrel;

FIGS. 2-6 illustrate seriatim the steps in coating the mandrel of FIG. 1 to form a sheath;

FIG. 15 is a sectional view of a second modified catheter; and

FIG. 16 is a sectional view of a third modified catheter.

DESCRIPTION OF THE PREFERRED EMBODIMENTS

The sheath of the catheter of the present invention may be formed directly on a catheter as is shown in FIGS. 1-6 or the sheath may be made on a mandrel for subsequent placement on a catheter as shown in FIGS. 7-11.

Figures 1, 2, 3:
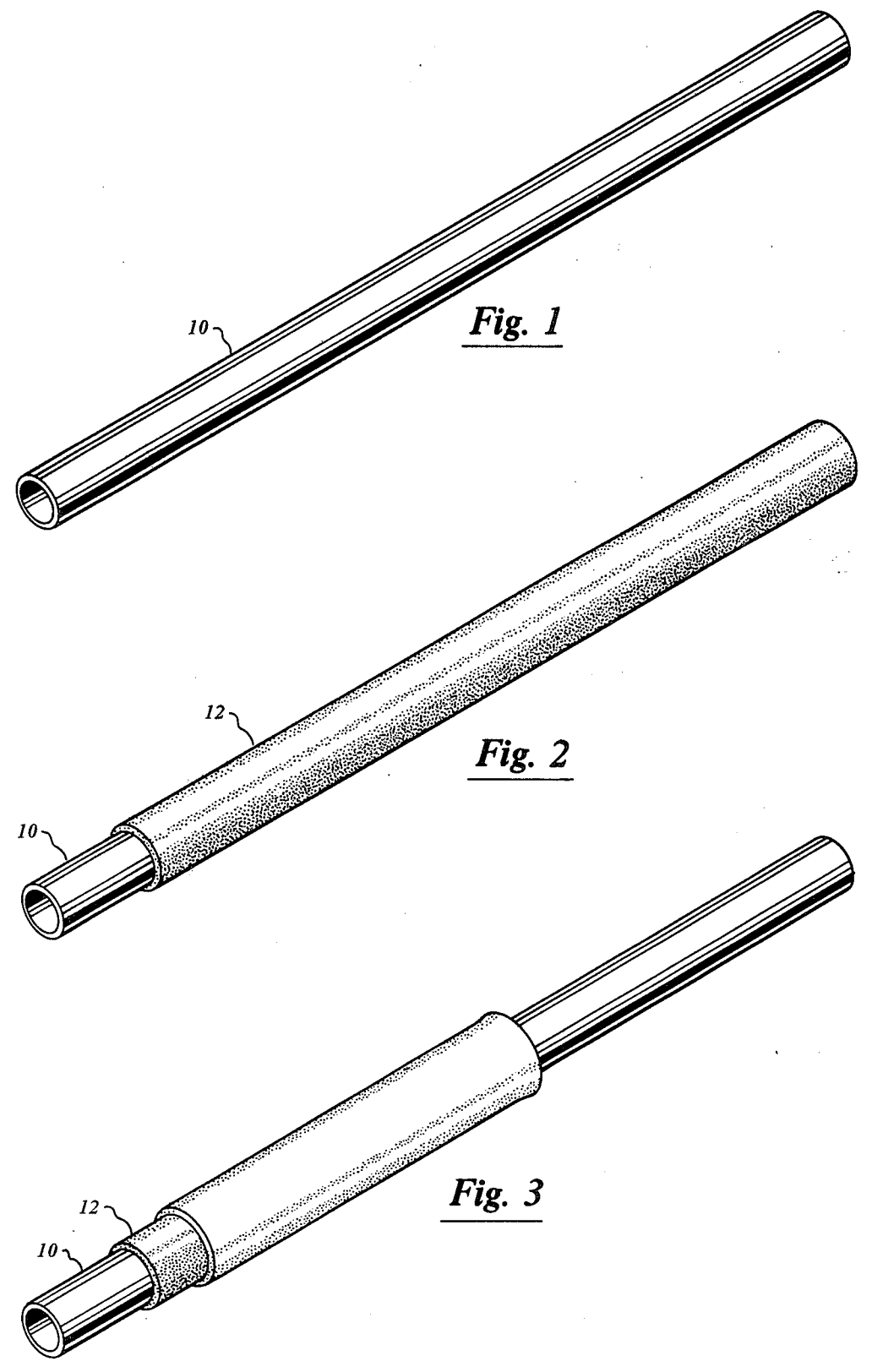
Figure 4:
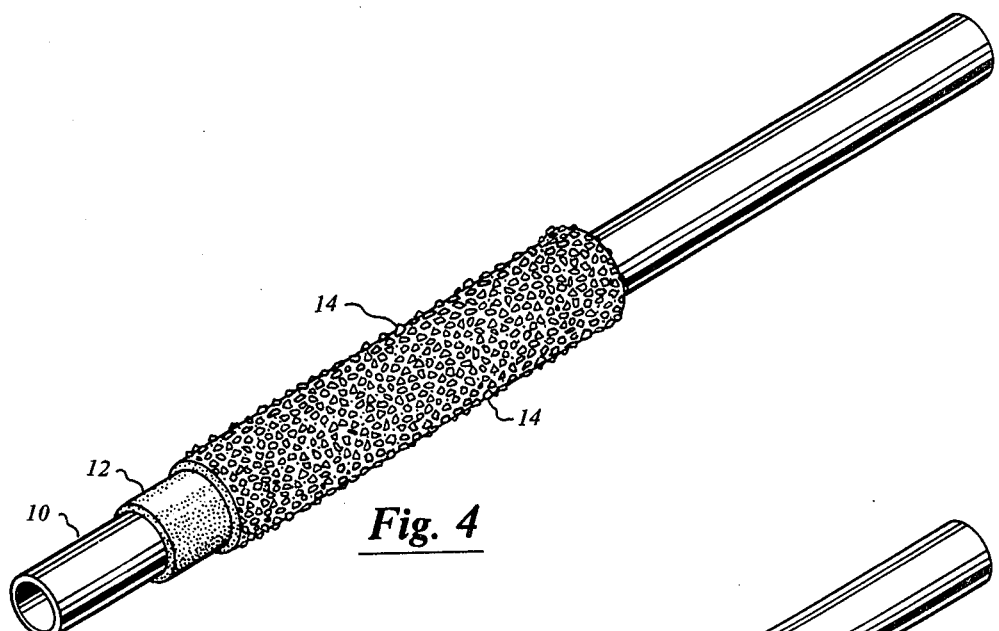
Figure 5:
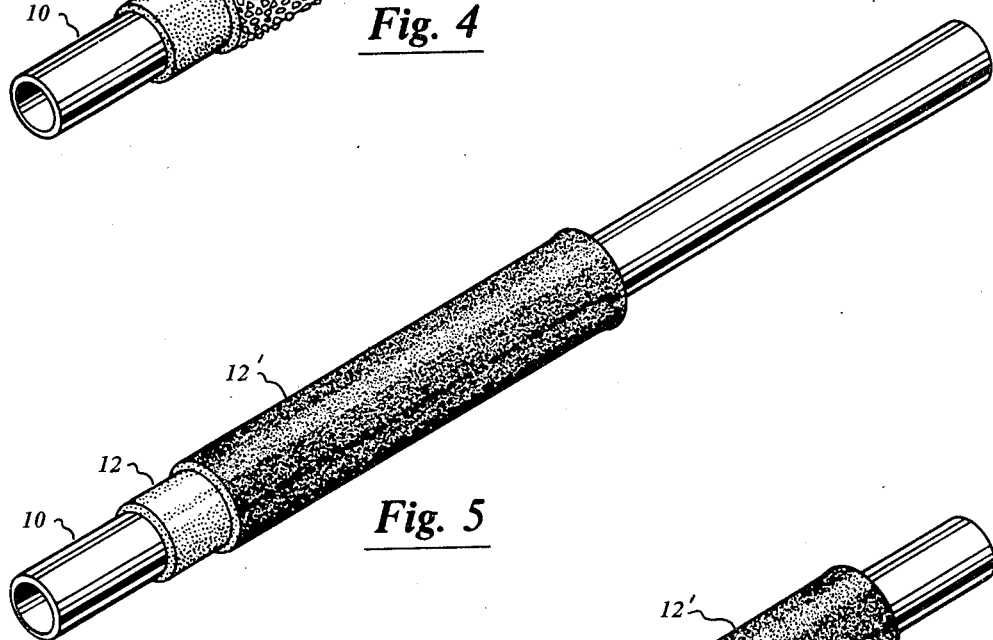
Figure 6:
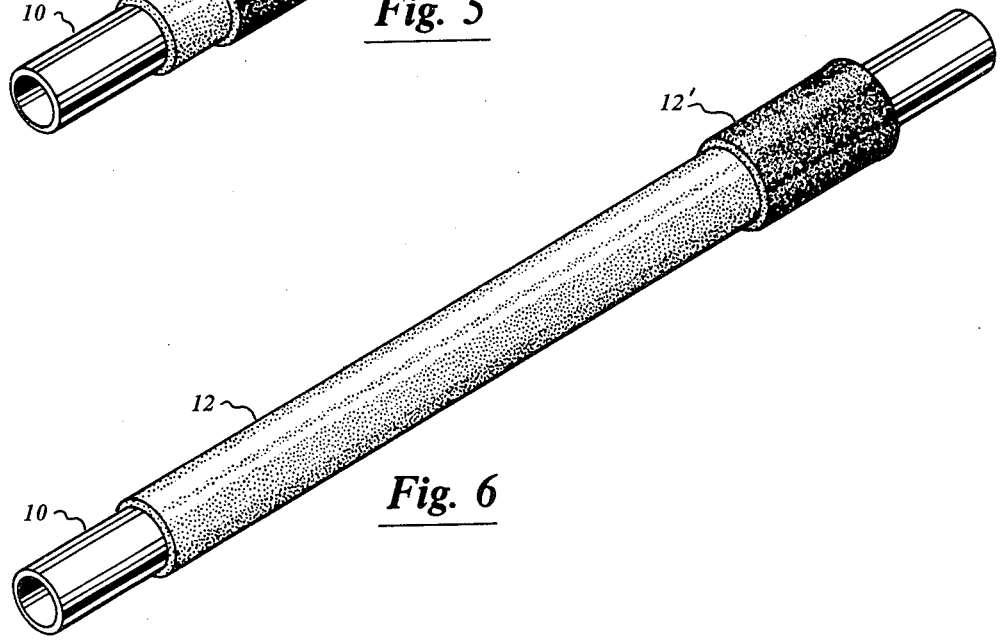

In FIG. 1 the numeral 10 designates a tubular mandrel which usually will be a portion of a catheter. As shown in FIG. 2, the mandrel 10 is coated with a sheath 12 of a segmented polyethertype polyurethane elastomer such as that sold by Johnson & Johnson under the trademark "Biomer". Through a sequential process of dipping the mandrel 10 in the coating solution and oven drying, a useful thickness of the sheath 12 is typically built up in two to four coats. The sheath 12 is then preferably coated with a silicone oil lubricant and folded back upon itself, as shown in FIG. 3, and is again dipped in the coating solution and, while still in a tacky state, is contacted with controlled-size particles such as 50-150 micron sodium chloride. The particles of sodium chloride 14 stick to the sheath 12 as shown in FIG. 4. The coated mandrel 10 is then oven dried and washed to remove the sodium chloride. As best shown in FIG. 5, the portion of the sheath 12 which had been in contact with the sodium chloride is designated 12' and is roughened and suitable for tissue ingrowth. Where mandrel 10 is a catheter, the roughened portion of the sheath 12' is then subjected to a conventional glow discharge treatment to clean as well as to raise the surface energy of roughened portion 12' which is then rolled back to form only a cuff as illustrated in FIG. 6. The mandrel/catheter 10 is then ready for packaging or implant. If mandrel 10 is not a catheter, the sheath 12 is removed from the mandrel 10 and placed on a catheter as described below.

Figure 7:
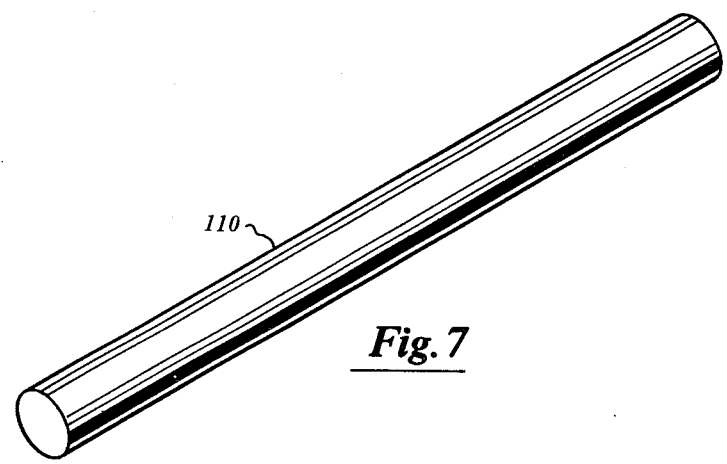
FIG. 7 is a pictorial view of a solid mandrel.
Figure 8:
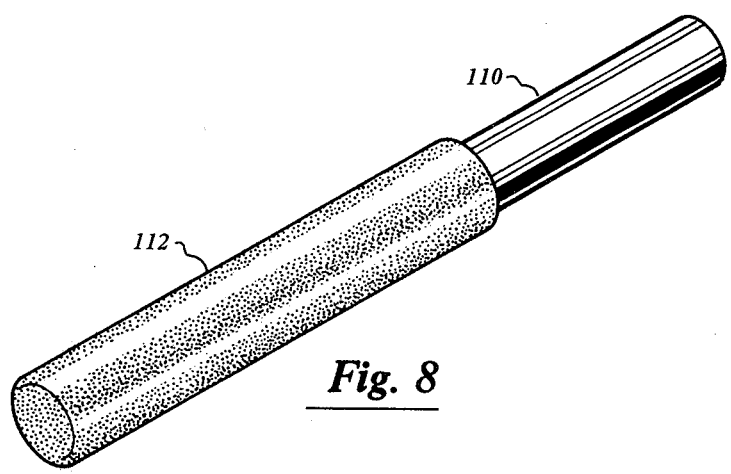
FIGS. 8-11 illustrate seriatim the steps in coating the mandrel of FIG. 7 to form a sheath.
Figure 9:
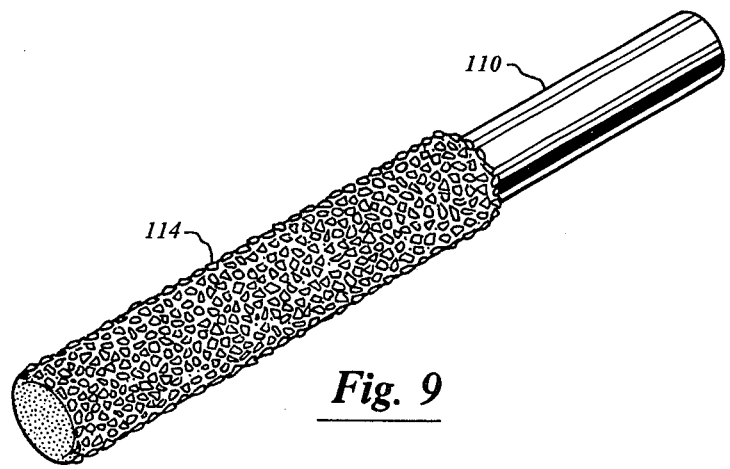
Figure 10:
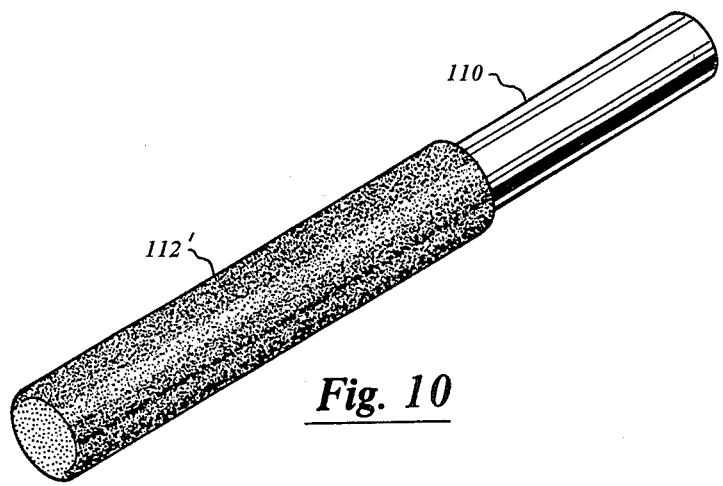
Figure 11:
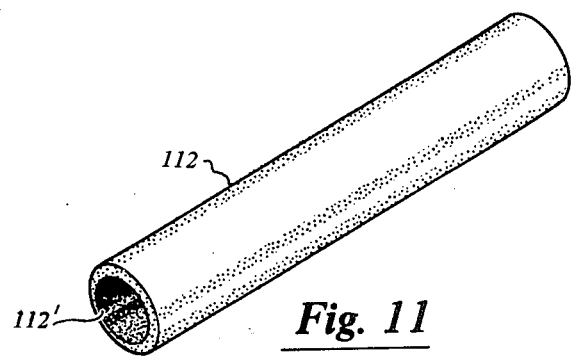
Figure 12:
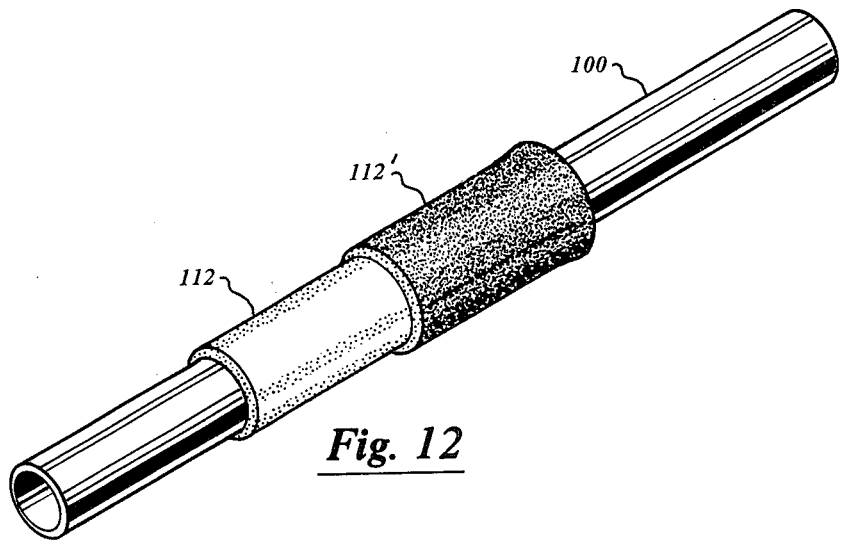
FIG. 12 illustrates the sheath of FIG. 11 on a catheter.

In FIG. 7 the numeral 110 designates a mandrel on which a sheath 112 is built up in a sequential process of dipping the mandrel 110 in the coating solution and oven drying, as described above, and illustrated in FIG. 8. The mandrel 110 is again dipped in the coating solution and, while still in a tacky state is contacted with controlled-size particles such as 50–150 micron sodium chloride. As shown in FIG. 9, the particles of sodium chloride 114 stick to the sheath 112. The coated mandrel 110 is then oven dried and washed to remove the sodium chloride. As best shown in FIG. 10 the portion of the sheath 112 which was in contact with the sodium chloride is designated 112' and is roughened and suitable for tissue ingrowth. The sheath 112 is then everted and removed from the mandrel 110, as shown in FIG. 11, the closed end of the sheath 112 is then removed and the sheath 112 is cut to a proper length so that an open tube results. The everted sheath 112 of FIG. 11 would correspond to the sheath 12 of FIG. 5 if removed from the mandrel 10. The everted sheath 112 would then be placed on a catheter 100 as illustrated in FIG. 12 and which corresponds to the sheath 12 on catheter/mandrel 10 of FIG. 6. The roughened surface 112' would then be subjected to a glow discharge treatment and rolled back to form a cuff. The catheter 100 would then be ready for packaging or implant.

Figure 13:
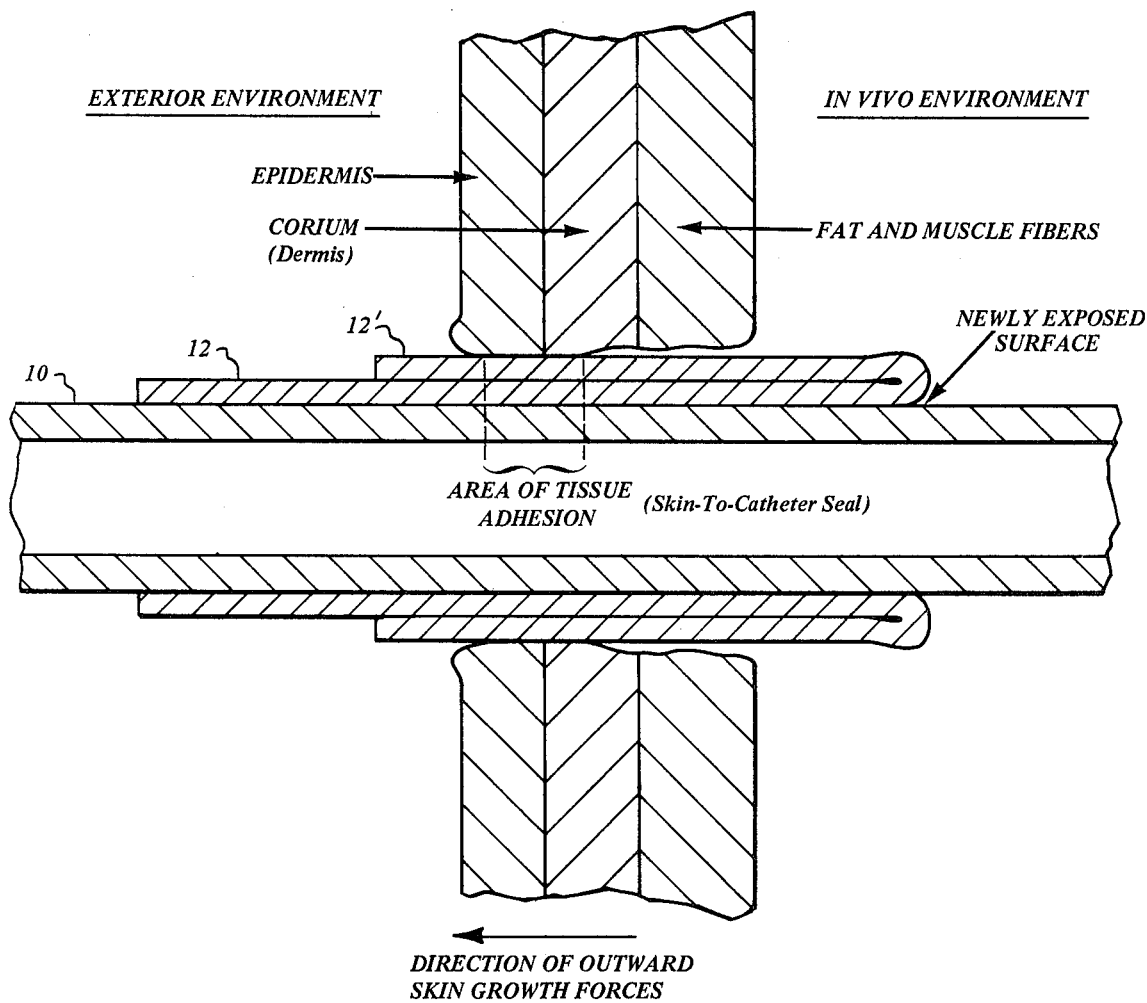
FIG. 13 is a sectional view showing the tissue coaction with the sheath of a catheter.

Although FIG. 13 illustrates the tissue coaction with roughened portion 12' of sheath 12 of the catheter 10 of FIG. 6, this would be equally true of the coaction with roughened portion 112' of the sheath 112 of catheter 100 of FIG. 12. An area of tissue adhesion occurs between the skin/tissue and a portion of the roughened surface 12'. Due to normal growth, the area of tissue adhesion will move outwardly at the rate of about 1 mm per month and the tissue will be sloughed off. Because the sheath 12 is folded back upon itself to form a cuff, only the cuff portion of the sheath 12 advances with tissue growth, assuming the catheter 10 is not free to move outwardly. The advancing sheath 12 continues to expose new surface area until the entire implanted portion of sheath 12 is moved outwardly through the skin, or until the catheter 10 is surgically removed from the patient. A coating of silicone oil between the contacting surfaces of the sheath 12 facilitates its outward movement.

Figure 14:
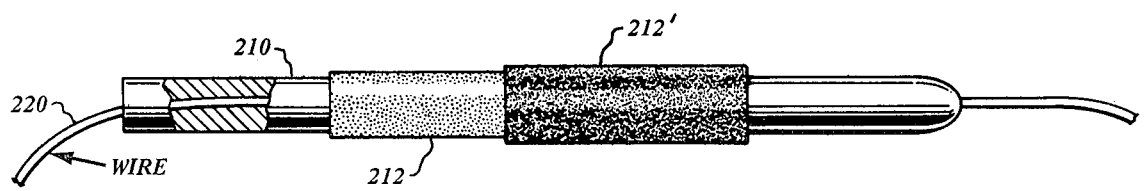
FIG. 14 is a partially sectioned view of a first modified catheter.

As shown in FIG. 14, the mandrel/catheter 210 may be solid silicone rubber and have suitable anchoring wires/electrical leads 220 embedded therein as for providing electrical power to an artificial organ such as a heart. The mandrel/catheter 210 has a sheath 212 having a roughened portion 212' thereon. If the catheter 210 is secured to the skeletal structure of the patient, the sheath 212 will be able to advance outwardly with the tissue growth while the catheter 210 remains in a fixed position. However, if the catheter 210 is not otherwise secured in place as by lead(s) 220, alternative anchoring structure must be provided to prevent outward movement of the catheter 210. Two forms of alternative anchoring structure are illustrated in FIGS. 15 and 16.

The catheter 310 of FIG. 15 is intended for placement in a patient in an area such as the abdomen which has no skeletal structure to which the catheter 310 can be secured. When catheter 310 is surgically emplaced, the interior end of the catheter is located in or at a natural or artificial organ 325 such as an artificial heart. Located on the interior end of the catheter 310, within the organ 325, is an inflatable collar 330 having an inflating tube 332 extending from the collar 330, through the catheter 310 to a source of inflation (not illustrated). After the surgical placement of catheter 310, the collar 330 is inflated and tube 332 is sealed to keep collar 330 in the inflated condition. As the adhering tissue moves outwardly, the cuff of sheath 312 is peeled back exposing new surfaces since inflated collar 330 tends to withstand any tendency to pull the catheter 310 out due to tissue growth.

The catheter 410 of FIG. 16 is intended for placement in a patient in an area such as the ribs, where the catheter 410 can be secured to the skeletal structure, such as bone 425, for which catheter 410 is provided with a flange 410a. Since the bone 425 coacting with flange 410a prevents the withdrawl of the catheter, the growth of the tissue advances the cuff of sheath 412 outwardly.

Although preferred embodiments of the present invention have been illustrated and described, other changes will occur to those skilled in the art. For example, in addition to the segmented polyether-type polyurethane elastomer, polyester-type polyurethanes such as "Estane", silicone rubber such as "Silastic", synthetic ruber such as polyhexene/"Hexsyn" or other elastomeric materials such as natural latex can be used. Additionally, the controlled-size particles may be urea, potassium hydrogen phosphate, water soluble polyelectrolytes ranging from gelatin to polyacrylamide or any substance in which you can control the dry size particles and which is water soluble. It is therefore intended that the scope of the present invention is to be limited only by the scope of the appended claims.

I claim:

1. A method for making a sheath for a catheter including the steps of:
   forming a cured elastomeric sheath on a mandrel;
   coating the sheath with elastomeric coating material;
   contacting the elastomeric coating material on the mandrel with solid, solvent-soluble particles while the elastomeric coating material is in a tacky state;
   curing the elastomeric coating material containing said particles;
   leaching said particles from the cured elastomeric coating material to produce a roughened surface suitable for tissue ingrowth;
   removing the coated sheath from the mandrel;
   trimming the sheath;
   placing the sheath on a catheter such that when the sheath is folded back to form a cuff, the roughened surface will form the outer surface of the cuff;
   folding back the sheath to form a relatively large cuff;
   glow discharge treating the external surface of the relatively large cuff; and
   pushing back the sheath to form a relatively smaller cuff whereby when the catheter is fixedly implanted in a body, tissue ingrowth will occur at the roughened outer surface of the cuff and the outward growth of the skin will peel back the cuff exposing new surfaces for tissue ingrowth while the catheter remains securely in place.

2. The method of claim 1 further including the step of lubricating the outer surface of the sheath before folding back the sheath to form a cuff.

3. The method of claim 1 wherein the elastomeric material is a segmented polyether-type polyurethane elastomer.

4. A method for forming a sheath on a catheter including the steps of:
   forming a cured elastomeric sheath on a catheter;
   folding back the sheath to form a relatively large cuff;
   coating the cuff with elastomeric coating material;

contacting the elastomeric coating material on the cuff with solid, solvent-soluble particles while the elastomeric coating material is in a tacky state;

curing the elastomeric coating material containing said particles;

leaching said particles from the cured elastomeric coating material to produce a roughened surface suitable for tissue ingrowth;

glow discharge treating the external surface of the relatively large cuff; and pushing back the sheath to form a relatively smaller cuff whereby when the catheter is fixedly implanted in a body, tissue ingrowth will occur at the roughened outer surface of the cuff and the outward growth of the skin will peel back the cuff exposing new surfaces for tissue ingrowth while the catheter remains securely in place.

5. The method of claim 4 further including the step of lubricating the outer surface of the sheath before folding back the sheath to form a cuff.

6. The method of claim 4 wherein the elastomeric material is a segmented polyether-type polyurethane elastomer.

7. A catheter for long-term emplacement including:

core means for the percutaneous transmission of energy or matter;

anchoring means for securing said core means in place; and an elastomeric sheath located on said core means and folded back to form a cuff having an outer surface roughened by leaching solid solvent-soluble particles from a coating on the outer surface of said cuff and further having been treated by glow discharge in order to render the outer surface of said cuff suitable for tissue ingrowth whereby when said catheter is fixedly implanted in a body by said anchoring means, tissue ingrowth will occur at the outer surface of the cuff and the outward growth of the skin will peel back said cuff exposing new surfaces for tissue ingrowth while the catheter remains securely in place.

8. The catheter of claim 7 wherein the sheath is made of a segmented polyether-type polyurethane elastomer.

* * * * *